United States Patent
Kishishita et al.

(10) Patent No.: US 6,444,251 B1
(45) Date of Patent: Sep. 3, 2002

(54) SWEETENER COMPOSITIONS CONTAINING ASPARTAME AND ASPARTAME DERIVATIVE

(75) Inventors: Akihiro Kishishita; Kazutaka Nagashima, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/594,039

(22) Filed: Jun. 15, 2000

Related U.S. Application Data

(63) Continuation of application No. PCT/JP98/05555, filed on Dec. 8, 1998.

(30) Foreign Application Priority Data

Dec. 15, 1997 (JP) ............................................. 9-344778

(51) Int. Cl.$^7$ ............................................. A23L 1/236
(52) U.S. Cl. ............................ 426/548; 426/89; 560/40
(58) Field of Search .......................... 426/548, 89, 96; 560/39, 40, 41

(56) References Cited

U.S. PATENT DOCUMENTS 5,480,668 A  1/1996  Nofre et al.

FOREIGN PATENT DOCUMENTS

JP  8-503206  4/1996

*Primary Examiner*—Leslie Wong
(74) *Attorney, Agent, or Firm*—Oblon, Spivak, McClelland, Maier & Neustadt, P.C.

(57) ABSTRACT

A homogeneous sweetener composition containing aspartame (APM) and N-[N-(3,3-dimethylbutyl)-L-α-aspartyl]-L-phenylalanine methyl ester having tasting properties similar to sucrose, can be efficiently produced in high yields and with a high purity by reductive alkylation of APM with an at most equimolar amount 3,3-dimethylbutyladehyde followed by separating the reducing agent from the liquid reaction mixture, and separating of the precipitated crystals of the sweetener composition.

13 Claims, No Drawings

SWEETENER COMPOSITIONS CONTAINING ASPARTAME AND ASPARTAME DERIVATIVE

This application is a continuation of PCT/JP98/0555, filed Dec. 8, 1998.

BACKGROUND OF THE INVENTION

1. Field of the Invention

The present invention relates to a sweetener composition and to a process for the production of the sweetener composition containing the sweetening substances aspartame (APM) and N-[N-(3,3-dimethylbutyl)-L-α-aspartyl]-L-phenylalanine methyl ester.

2. Discussion of Background Art

Awareness of fatness, caused by excessive sugar intake and diseases accompanied by fatness, has increased as eating habits have improved in recent years. Accordingly, there has been a need for the development of a low-calory sweetening agent (sweetener) that replaces sugar. Aspartame (APM) is widely used as a sweetening agent because of its excellent safety and quality of sweetness. However, aspartame is not very stable.

French Patent No. 2697844 discloses a derivative in which an alkyl group is introduced into an amino group of aspartic acid. It was shown that N-[N-(3,3-dimethylbutyl)-L-α-aspartyl]-L-phenylalanine methyl ester, which hereinafter is abbreviated to "N-(3,3-dimethylbutyl)-APM", or simply referred to as "APM derivative", exhibits improved stability and a markedly improved sweetening potency. Processes for the production of N-(3,3-dimethyl-butyl)-APM are known. For example, FR 2697844 describes a process for the reductive alkylation of APM in the presence of 3,3-dimethylbutylaldehyde and sodium cyanoborohydride in methanol. In WO95/30689, APM is reductively alkylated in the presence of 3,3-dimethylbutylaldehyde and platinum carbon as the catalyst in a mixed solvent of water and methanol at a pH of 4.5 to 5. However, when the reaction is carried out according to the processes described in the above patents, 3,3-dimethylbutylaldehyde does not react completely with APM and a byproduct, N-[N,N-di-(3,3-dimethylbutyl)-L-α-aspartyl]-L-phenylalanine methyl ester having two alkyl groups, is produced.

The sweetening potencies of N-(3,3-dimethylbutyl)-APM and aspartame (APM) are reported to be 10,000 times (Japanese Patent Kohyou Publication JP-A-8-503206) and about 200 times (Japanese Patent Kokoku Publication JP-B-47-31031) that of sucrose, respectively.

The quality of sweetness of N-(3,3-dimethylbutyl)-APM is not reported in detail, however, it is extremely weak in early taste and extremely strong in later taste. Early taste and late taste are determined in comparison to sucrose. For example, a sweetener, when put in the mouth, can taste sweet as early as sucrose or later than sucrose. N-(3,3-dimethylbutyl)-APM is strong in astringency (astringent taste) and badly balanced for quality of sweetness compared to sucrose. APM is weak in early taste and strong in later taste, although improved compared to N-(3,3-dimethylbutyl)-APM. Both compounds have a quality of sweetness which is weak in early taste and strong in later taste based on sucrose.

There have been various proposals for the improvement of particularly the later taste (see, e.g., Japanese Patent Kokai Publication JP-A-56-148255, JP-A-58-141760, JP-A-58-220668, etc.). Furthermore, among the proposals are methods for obtaining a natural quality of sweetness closer to that of sucrose, for example, by the combination with sucrose (Japanese Patent Kokai Publication JP-A-57-152862).

According to the findings of the inventors, it is possible to intensify early taste, weaken later taste and to weaken the astringent taste, thereby balancing the quality of sweetness by combining N-(3,3-dimethylbutyl)-APM and APM homogeneously. A homogeneous composition of N-(3,3-dimethylbutyl)-APM and APM is improved in early taste and expected to give a high degree of sweetness as well as a balanced quality of sweetness closer to that of sucrose, compared to its singly used ingredients N-(3,3-dimethylbutyl)-APM or APM.

It is somewhat difficult to adjust the degree of sweetness when using N-(3,3-dimethylbutyl)-APM because its sweetening potency is 10,000 times (Japanese Patent Kohyou Publication JP-A-8-503206) that of sucrose. Accordingly, a combination of N-(3,3-dimethylbutyl)-APM with APM not only improves the quality of sweetness, but is also allows easy adjustment of the degree of sweetness.

SUMMARY OF INVENTION

It is an object of the present invention to provide a process for producing a homogeneous sweetener composition containing APM and N-(3,3-dimethylbutyl)-APM in high yields and with a high purity. An improved quality of sweetness compared to mixtures of crystals of APM and crystals of APM derivative is desired. It is another object of the present invention to provide a sweetener composition obtained by the process according to the invention.

These and other objects are achieved according to the invention, the first embodiment of which includes a process for production of a sweetener composition, comprising:

reductively alkylating aspartame and 3,3-dimethylbutylaldehyde in an amount of 3,3-dimethylbutylaldehyde at most equimolar to the aspartame in the presence of a reducing agent in a reaction solution to form a sweetener composition; separating said reducing agent from said reaction solution; crystallizing said sweetener composition and isolating a precipitated sweetener composition.

Another embodiment of the invention includes the sweetener composition produced by the above process and comprising aspartame and N-[N-(3,3-dimethylbutyl)-L-α-aspartyl]L-phenylalanine methyl ester.

Another embodiment of the invention includes the sweetener composition comprising a homogeneous composition of aspartame and N-[N-(3,3-dimethylbutyl)-L-α-aspartyl]-L-phenylalanine methyl ester, wherein said sweetener composition does not contain N-[N,N-di(3,3-dimethylbutyl)-L-α-aspartyl]-L-phenylalanine methyl ester.

DETAILED DESCRIPTION OF THE INVENTION

The present inventors have found that N-[N-(3,3-dimethylbutyl)-L-α-aspartyl]-L-phenylalanine methyl ester (N-(3,3-dimethylbutyl)-APM)) can be produced by reductive alkylation using, for example, 1 mol of APM and an at most equimolar amount of the 3,3-dimethylbutylaldehyde to APM, i.e. 1 mole or less of 3,3-dimethylbutylaldehyde. The amount of 3,3-dimethylbutylaldehyde is preferably about 0.0003–0.28 mol, and more preferably about 0.0005–0.25 mol for 1 mol of APM. The amount of 3,3-dimethylbutylaldehyde includes all values therebetween, especially including 0.0003, 0.0004, 0.0008, 0.001, 0.002, 0.005, 0.007, 0.009, 0.011, 0.02, 0.05, 0.07, 0.09, 0.11, 0.13, 0.15, 0.17, 0.19, 0.21, 0.23, 0.25, 0.27 and 0.28 mol for 1 mol of APM.

After completion of the alkylation reaction, the reducing agent is separated from the reaction mixture. Crystallization is affected and followed by the separation of the precipitated crystals. An excellent sweetener composition containing aspartame (APM) and N-[N-(-3,3dimethylbutyl)-L-α-aspartyl]-L-phenylalanine methyl ester and having a balance in quality of sweetness can be easily and efficiently produced in high yields and with high purity without producing N-[N,N-di(3,3-dimethylbutyl)-L-α-aspartyl]-L-phenylalanine methyl ester as a by-product. The obtained sweetener composition is superior to those produced by simply mixing crystals of APM and crystals of the APM derivative.

A sweetener composition containing APM and the APM derivative obtained by the process according to the present invention, may be preferable as a sweetener. More preferably, the dried form is used as a sweetener. The sweetener can contain a carrier, if required. A suitable carrier can be produced or selected through the known methods for production or selection of carriers. The sweetening composition can be used as a sweetener or as a sweetening agent. Various products can be sweetened with the composition of the present invention, for example, food, cosmetics (dental rinse, mouth wash, etc.) and oral pharmaceuticals. APM and the APM derivative can be contained in the sweetener composition in a weight ratio of 0.05–50, preferable 1–40, more preferably 5–30 of the APM derivative per 100 of the APM. The weight ratio includes all values therebetween, especially including 0.05, 0.1, 0.5, 1, 5, 10, 15, 20, 25, 30, 35, 40, 45 and 50.

Preferred, catalysts for the reductive alkylation are platinum-carbon, palladium-carbon, platinum black, palladium black, etc. (WO95/30689). However, the catalyst is not limited to these species. After completion of the reductive alkylation, the catalyst is separated from the solution containing APM and the APM derivative. The remaining solution is concentrated, if required. The crystals precipitate and are separated, yielding a sweetener composition containing homogeneous APM and the APM derivative.

Preferred solvents are water, ethyl acetate, methyl acetate, acetic acid, toluene, hexane, tetrahydrofuran, acetonitrile, dimethoxyethane, ethyl ether, isopropyl alcohol, ethyl alcohol, methyl alcohol, dichloromethane, chloroform and 1,2-dichloroethane, or mixtures thereof.

Concentration of the reaction solution before crystallization may be required to increase the yield. Therefore, it is preferable to employ an alcohol based solvent or a mixed solvent during the reaction. Preferably, water or a mixture of water and alcohol based solvent(s) is employed. The alcohol based solvent or the mixed solvent is replaced by water to allow to easily minimize the solvent in the final product. The replacement is achieved by adding a suitable amount of water to the reaction solution, and then concentrating the same.

The desired amount of APM in the composition is obtained by adjusting, for example, the amount of 3,3-dimethylbutylaldehyde, the reaction temperature or the reaction time. In addition, the weight ratio can be controlled by adding APM in an amount that exceeds the limit of its solubility before starting the reaction, and then dissolving the excess APM, for example, by heating before the separation of the catalyst. Furthermore, control of the weight ratio is possible by adding a suitable amount of APM to the reaction solution after the separation of the catalyst and dissolving the added APM. Furthermore, APM can be dissolved in the reaction solvent before starting the reaction. Alternatively, a slurry of APM may be empoloyed.

Crystallization of the composition from the reaction solution may be initiated by, for example, cooling, concentrating, or neutralizing. It is known that refined crystals may be formed under stirring. If an excess of APM has been used, the solution may be subjected to crystallization under standing (static crystallization) or to crystallization under stirring or a combination of these procedures (Japanese Patent Kokoku Publication JP-B-03-025438).

The sweetener composition can be obtained by separating the liquid and the solid material of the obtained slurry (sherbet). The solid material is then dried and granulated (pelletized), if required. Preferably, the solid material is separated from the liquid by filtration or centrifugation. The solid material may be washed after the separation. Preferably, drying can proceed by using a vacuum dryer, a fluidized-bed dryer, a spray dryer, or a micron dryer. Preferably, the granulation is achieved by dry granulating or wet granulating. However, there is no limitation to these exemplified methods.

It is an advantage of the process of the present invention to give a homogeneous composition of APM and the APM derivative. Such homogeneity is difficult to achieve when mixing separately produced APM and APM derivative crystals. The homogeneous composition does not contain N-[N,N-di(3,3-dimethylbutyl)-L-α-aspartyl]-L-phenylalanine methyl ester. Preferably, it contains N-[N,N-di(3,3-dimethylbutyl)-L-α-aspartyl]-L-phenylalanine methyl ester in an amount of less than 5%, more preferably less than 2.5%, even more preferably less than 1% and most preferably less than 0.5%.

Having generally described this invention, a further understanding can be obtained by reference to certain specific examples which are provided herein for purposes of illustration only, and are not intended to be limiting unless otherwise specified.

EXAMPLES

Example 1

APM (aspartame; 55.0 g, 0.180 mol) with a water content of 3.9% by weight and 3,3-dimethylbutylaldehyde (2 ml, 0.016 mol) were added to water (1000 ml) and the resulting solution was maintained at 23° C. 5% palladium-carbon (5.0 g) were added, and the solution was subjected to a reductive reaction for 2 hours under a flow of hydrogen ($H_2$) at a flow rate of 100 ml per 1 hour. After that, the flowing of hydrogen was terminated, and the solution was heated to 69° C. to completely dissolve the undissolved crystals. The catalyst was removed by filtration with a filter paper of 0.5 micrometer ($\mu$m), and the resulting filtrate was allowed to stand for static crystallization at 5° C. for 4 hours. The resulting pseudo-solid phase (sherbet) was maintained overnight at 5° C. under stirring to prepare a slurry. The resulting slurry was filtrated through a filter paper of 5 $\mu$m to separate the solid phase from the liquid phase. The solid phase was washed with 250 ml of water, and dried under reduced pressure at 50° C. overnight to obtain 43.6 g of the dried crystals with a water content of 2.7% by weight (APM: 95.8 weight %; N-(3,3-dimethylbutyl)-APM: 2.5 weight % as determined by HPLC). Analysis of the composition by the thin layer chromatography (TLC) did not show any dialkylated by-product (i.e., N-[N,N-di(3,3-dimethylbutyl)-L-α-aspartyl]-L-phenylalanine methyl ester). The production of the by-product is reduced by using the APM in an amount at least equimolar to the 3,3-dimethylbutylaldehyde. The resulting composition was homogeneous (uniform) and was improved in quality of sweetness giving an excellent taste as a sweetener.

The sweetener composition containing APM and the APM derivative is improved in tasting properties and can be efficiently produced in high yields and with a high purity. These advantages are not achieved when merely uniting crystals of APM and the APM derivative.

The priority document of the present application, Japanese patent application, 9-344778, filed Dec. 15, 1997 and PCT application, PCT/JP98/05555, filed Dec. 8, 1998, are incorporated herein by reference.

Obviously, numerous modifications and variations on the present invention are possible in light of the above teachings. It is therefore to be understood that within the scope of the appended claims, the invention may be practiced otherwise than as specifically described herein.

We claim:

1. A sweetener composition, comprising aspartame and N-[N-(3,3-dimethylbutyl)-L-α-aspartyl]-L-phenylalanine methyl ester, wherein said sweetener composition is prepared by a process comprising:

reductively alkylating aspartame with 3,3-dimethylbutylaldehyde in the presence of a catalyst in a reaction solution to form a sweetener composition;

separating said catalyst from said reaction solution;

crystallizing said sweetener composition; and isolating a precipitated sweetener composition, wherein said aspartame is reductively alkylated with said 3,3-dimethylbutylaldehyde so that said sweetener composition comprises said N-[N-(3,3-dimethylbutyl)-L-α-aspartyl]-L-phenylalanine methyl ester and said aspartame in a weight ratio of 0.05 to 40 of said N-[N(3,3-dimethylbutyl)-L-α-aspartyl]-L-phenylalanine methyl ester to 100 of said aspartame.

2. The sweetener composition according to claim 1, wherein said sweetener composition is dry.

3. The sweetener composition according to claim 1, further comprising a carrier.

4. The sweetener composition according to claim 1, wherein said N-[N(3,3-dimethylbutyl)-L-α-aspartyl]-L-phenylalanine methyl ester and said aspartame are present in a weight ratio of 5 to 30 of said N-[N-(3,3-dimethylbutyl)-L-α-aspartyl]-L-phenylalanine methyl ester to 100 of said aspartame.

5. The sweetener composition according to claim 1, wherein said sweetener composition does not contain N-[N,N-di(3,3-dimethylbutyl)-L-α-aspartyl]-L-phenylalanine methyl ester.

6. The sweetener composition according to claim 1, wherein in said process said catalyst is selected from the group consisting of platinum carbon, palladium carbon, platinum black, palladium black, and mixtures thereof.

7. The sweetener composition according to claim 1, wherein in said process said reaction solution comprises a solvent selected from the group consisting of water, ethyl acetate, methyl acetate, acetic acid, toluene, hexane, tetrahydrofuran, acetonitrile, dimethoxyethane, ethyl ether, isopropyl alcohol, ethyl alcohol, methyl alcohol, dichloromethane, chloroform and 1,2-dichloroethane, and mixtures thereof.

8. The sweetener composition according to claim 1, wherein said process further comprises adding water prior to said crystallizing said sweetener composition.

9. The sweetener composition according to claim 1, wherein in said process said isolating is carried out by filtration or centrifugation.

10. The sweetener composition according to claim 1, wherein said process further comprises drying said precipitated sweetener composition.

11. The sweetener composition according to claim 10, wherein said drying is selected from the group consisting of vacuum drying, a fluidized-bed drying, a spray drying, and micron-drying.

12. The sweetener composition according to claim 1, wherein said process further comprises granulating said precipitated sweetener composition.

13. The sweetener composition according to claim 12, wherein said granulating is wet granulating or dry granulating.

* * * * *